United States Patent [19]
Gysi et al.

[11] Patent Number: 5,708,221
[45] Date of Patent: Jan. 13, 1998

[54] APPARATUS FOR THE INSPECTION OF CONTAINERS

[75] Inventors: Peter Gysi, Bellikon; Theo Huesser, Rudolfstetten, both of Switzerland; Thaddäus Jasny, Wiesbaden, Germany; Martin Rosatzin, Dietikon, Switzerland

[73] Assignee: Elpatronic AG, Zug, Switzerland

[21] Appl. No.: 610,761

[22] Filed: Mar. 5, 1996

[30] Foreign Application Priority Data

Apr. 3, 1995 [CH] Switzerland .......... 00927/95
Apr. 7, 1995 [CH] Switzerland .......... 00999/95

[51] Int. Cl.$^6$ .................................................. G01N 1/00
[52] U.S. Cl. .................................................. 73/864.81
[58] Field of Search .......... 73/863.31–863.33, 73/863.83, 864.34, 864.81; 209/522, 523; 356/36; 250/288; 137/625.41, 625.46, 627, 597, 862

[56] References Cited

U.S. PATENT DOCUMENTS 5,365,771  11/1994  Gysi et al. ................... 73/31.03
5,520,060  5/1996   Gysi et al. ................... 73/865.8

FOREIGN PATENT DOCUMENTS 0579952  6/1993  European Pat. Off. .

OTHER PUBLICATIONS

Journal of Vacuum Science Technology, A 4(3), May/Jun. 1986, USA, pp. 306–309, XP002007678 Ellefson et al.: "Central gas analysis laboratory with remote sampling" p. 306, col. 2, lines 18–22; fig. 2.

*Primary Examiner*—Robert Raevis
*Attorney, Agent, or Firm*—McCormick, Paulding & Huber

[57] ABSTRACT

On a distributor head for distributing gas samples removed from bottles requiring inspection to the connections for two mass spectrometers, the feed passageways form alternative paths. These different paths are contained in a replaceable part or a switchable valve arrangement. This allows easy changeover from operation with two mass spectrometers to operation with one mass spectrometer, so facilitating servicing of the mass spectrometers.

6 Claims, 5 Drawing Sheets

1

APPARATUS FOR THE INSPECTION OF CONTAINERS

BACKGROUND OF THE INVENTION

The invention relates to an apparatus for the inspection of containers, particularly bottles, which are transported on a carousel conveyor and from which gas samples are taken to check for contamination.

Such an apparatus is known from EP-A 0579952, which corresponds to U.S. Pat. No. 5,365,771 and is assigned to the assignee of the present invention. In the apparatus described in that publication, the lines running from the sampling probes to the distributor head are connected to the moving part of the distributor head in two concentric circles. Two testing instruments, usually mass spectrometers, are connected to the fixed part, each being permanently assigned to one of the circles of connections. With the apparatus known from EP-A 0579952, operation is possible only when both mass spectrometers are functioning. If one of the instruments need servicing, the apparatus is immobilized.

SUMMARY OF THE INVENTION

The principal object of the invention is to avoid this drawback. This is achieved, in an apparatus of the above-mentioned kind, by modifying the connections from the fixed part of the distributor head to the mass spectrometers to enable either or both of the spectrometers to be used.

By enabling a single mass spectrometer to be optionally connected to both circles of connections, it becomes possible to inspect all bottles with a single test instrument or mass spectrometer. If a second mass spectrometer is provided, it can be serviced, and, after it has been serviced, operation with two mass spectrometers can easily be restored. If desired, it is also possible to operate with one mass spectrometer for an extended period until it becomes necessary to increase the bottle throughput, when the second mass spectrometer can easily be brought into use.

BRIEF DESCRIPTION OF THE DRAWINGS

Embodiments of the invention will now be described in detail, by way of example, with reference to the drawings, in which.

DESCRIPTION OF THE PREFERRED EMBODIMENTS

Figure 1:
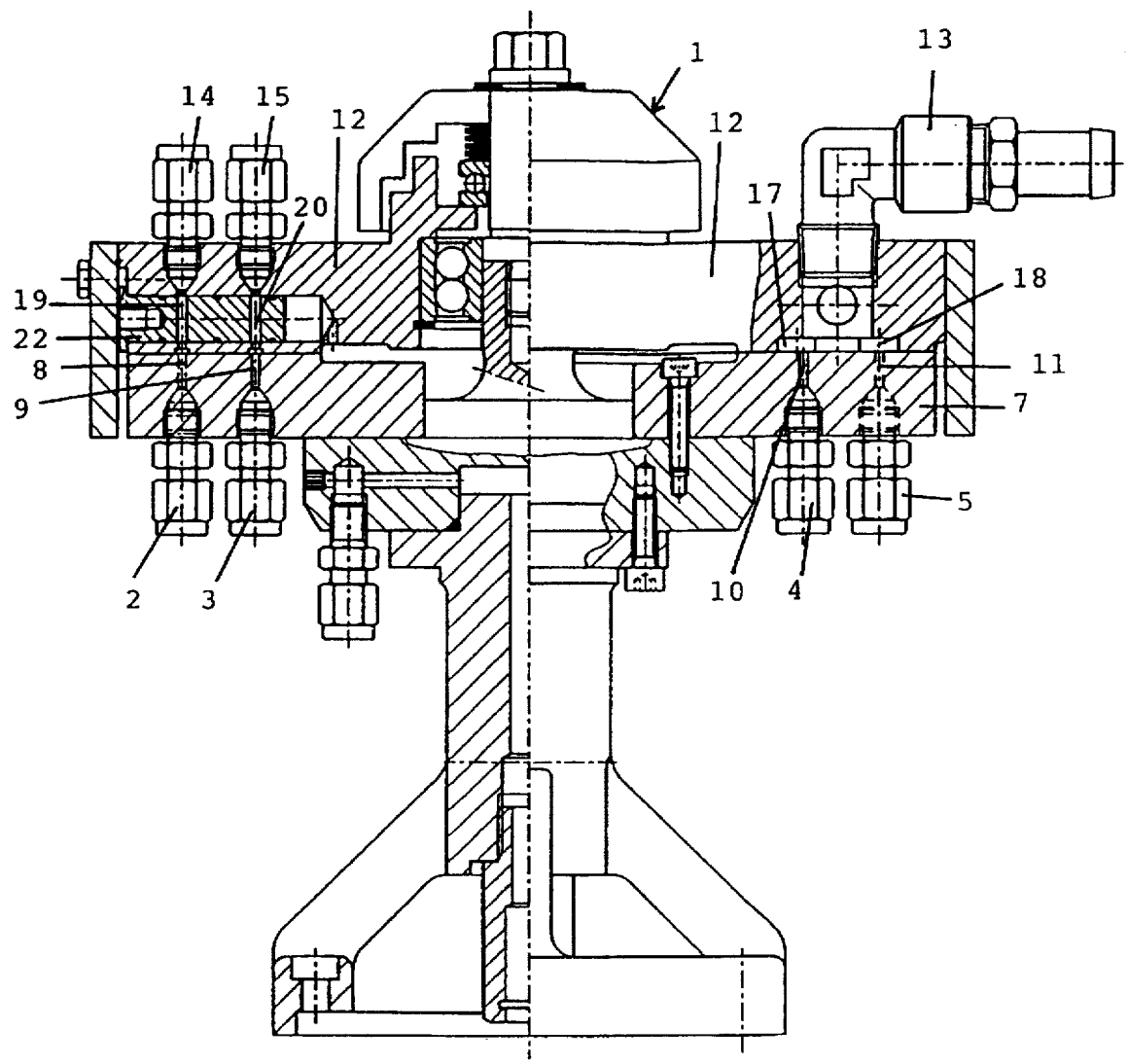
FIG. 1 is a view, partly in section, of a distributor head.
Figure 2:
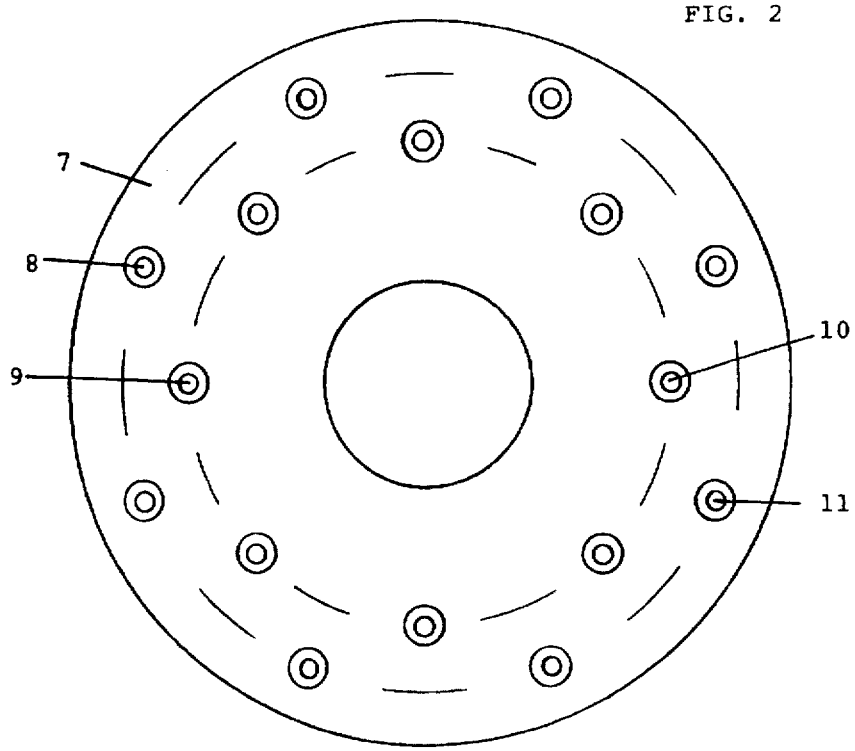
FIG. 2 is a top view of the rotating disk of the distributor head.
Figure 3:
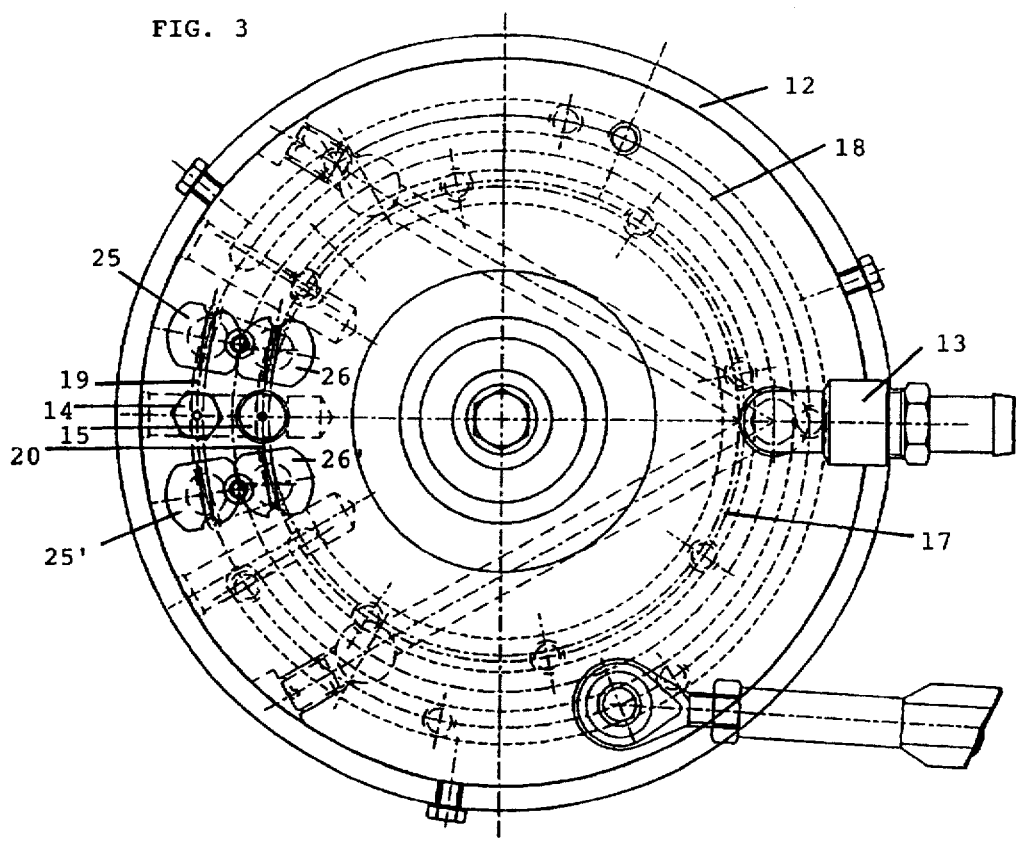
FIG. 3 is a view of the fixed disk of the distributor head.

FIG. 1 shows a distributor head for the gas samples withdrawn from the bottles to be inspected, basically as known from EP-A 579952. The bottles run in a carousel (not shown) arranged underneath the distributor head, and sampling probes dip into the bottles to remove samples of gas. These gas samples pass via pipes and connections, four of which (2, 3, 4, 5) can be seen in FIG. 1, to the lower disk 7 of the distributor head, which rotates with the carousel. FIG. 2 is a top view of this disk, showing the arrangement of the connections and of the corresponding passageways (8, 9, 10, 11 in FIG. 1) in the disk. The upper disk 12 of the distributor head, which is fixed, has a suction connection 13 leading to a suction pump (not shown) and two connections 14 and 15 each for a pipe leading to the respective inlet of a mass spectrometer, of which there are two (these are not shown in the drawings). The suction connection communicates with two concentric suction chambers 17 and 18. In FIG. 3, these suction chambers 17 and 18 are represented by broken lines. It will be seen that the suction connection communicates with the chambers 17 and 18 at three points. This is preferable to a single point of communication. The suction chambers extend almost around the entire disk, but stop short of a sector in which the connections 14 and 15 for the mass spectrometers are located and in which two passageways 19 and 20 assigned to these connections extend.

The function of the distributor head is basically similar to that of the distributor head known from EP-A 0579952, U.S. Pat. No. 5,365,771. At any given time, two connections (2, 3 in FIG. 1) are in communication via the passageways 19 and 20 with the connections 14 and 15 ie. with the mass spectrometers, and the individual gas samples pass to the mass spectrometers. At the same time all other connections (4, and 5 in FIG. 1) are in communication with the suction pump via the passageways 17 and 18, so that gas is drawn into the distributor head from the bottles coupled to them. Upon further rotation of the lower disk 7 with respect to the fixed upper disk 12, the next two connections are then brought into communication with the passageways 19 and 20 and the gas samples pass from the corresponding bottles to the mass spectrometers etc. Thus the action of the distributor head means that at any given time two adjacent gas samples are being routed to the two mass spectrometers, while gas samples are being extracted from the other bottles and are being made ready for transmission to the mass spectrometers.

Figure 5:
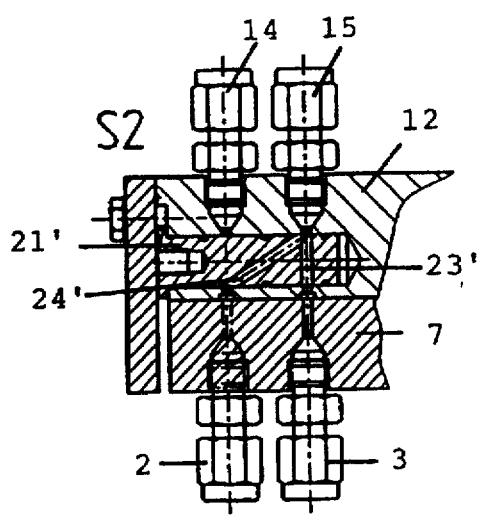
FIG. 5 is a detail view, partly in section, of the distributor head, with a second embodiment of the distributor plug.
Figure 4:
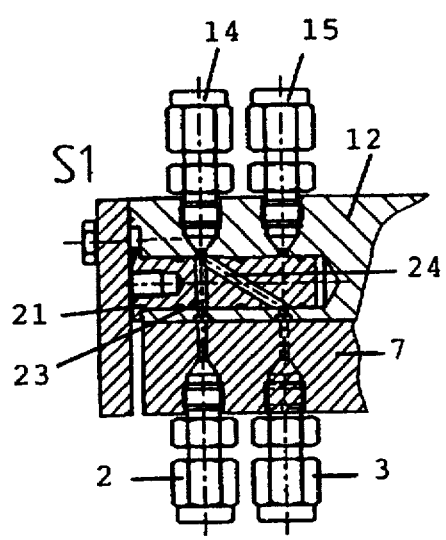
FIG. 4 is a detail view, partly in section, of the distributor head, with a first embodiment of the distributor plug.

In the example shown, the passageways 19,20 are arranged in a replaceable plug 22 which is inserted laterally into the fixed disk 12. The plug 22 can be removed and replaced by a plug 21 having a different arrangement of passageways 23,24, as seen in FIG. 4, which shows a detail view of the distributor head 1, with the same reference numbers designating the same parts as before. Here, the passageways 23,24 are formed so that the gas samples pass only to the mass spectrometer communicating with the connection 14. The mass spectrometer communicating with the connection 15 is therefore not in use, and can be serviced or repaired. FIG. 5 shows another embodiment with a plug 21' and passageways 23' and 24', with gas samples passing to the mass spectrometer communicating with the connection 15. To prevent the gas samples from the connections 2,3 from reaching the mass spectrometer simultaneously, it is necessary to shorten the passageways 19 and 20 in the example shown, so that the angular offset of the connections (cf. FIG. 2) between the two concentric circles of connections is sufficient to ensure a sequential feed of gas samples from the two circles of connections to the single mass spectrometer.

Figure 6:
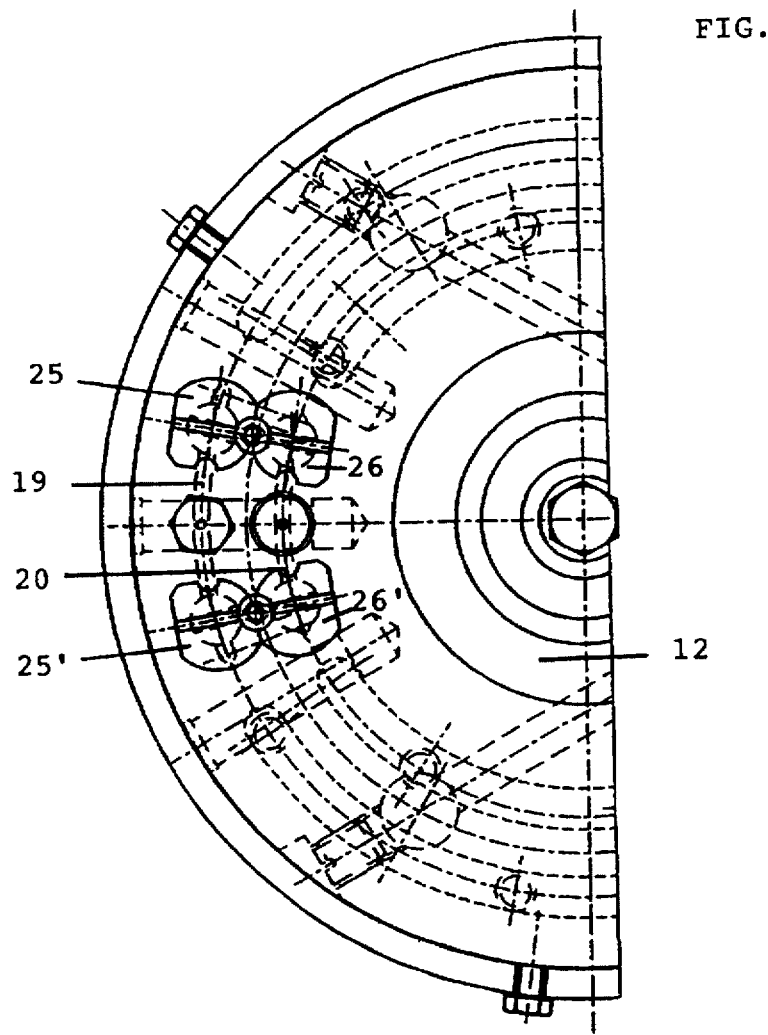
FIG. 6 is a partial view of the fixed disk for the embodiments shown in FIGS. 4 and 5.

FIG. 6 shows the shortening of the passageways 19,20 by means of studs 25,26 and 25',26', inserted in the disk 12, which form part of the passageways 19 and 20 respectively, and can be turned about a vertical axis (parallel with the carousel axis) so that the respective passageways 19 and 20 is lengthened or shortened. FIG. 6 shows the setting with short passageways; FIG. 3, the setting with long passageways.

Figure 7:
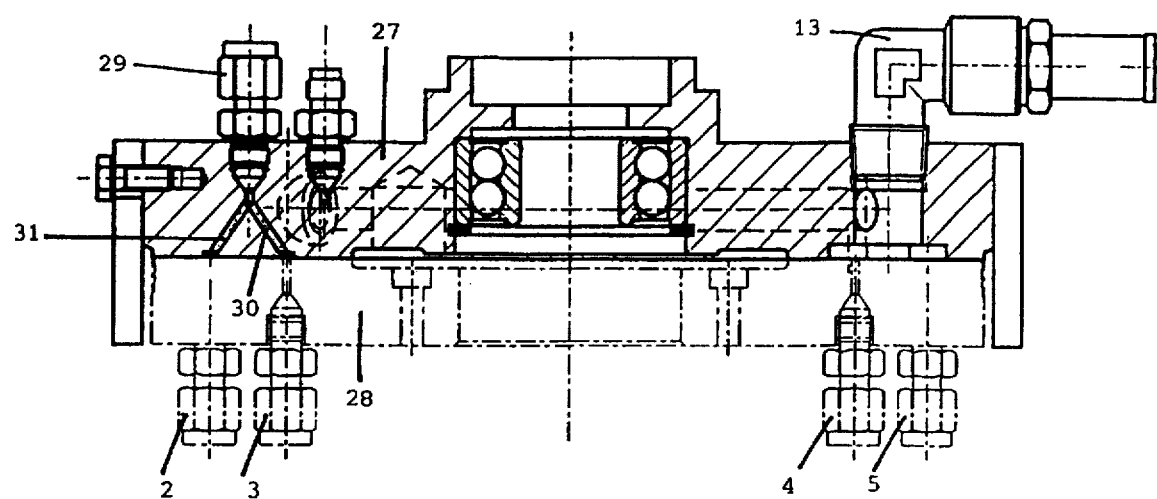
FIG. 7 shows one embodiment of the fixed part of the distributor head, drawn partly in section.
Figure 8:
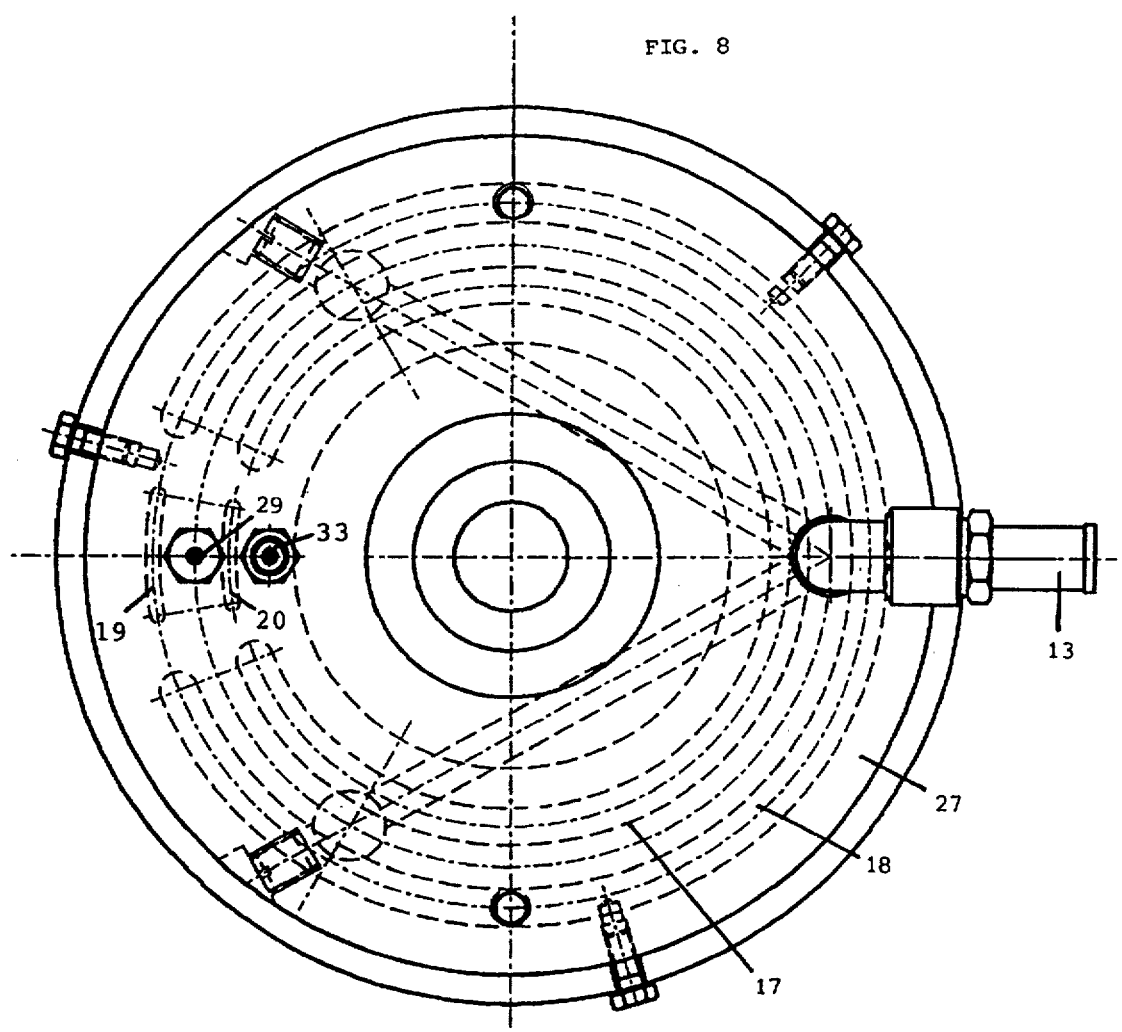
FIG. 8 is a view of the fixed part of the distributor head according to the embodiment in FIG. 7.

FIG. 7 shows a further embodiment of the invention, illustrating the upper, fixed disk 27 of the distributor head in a partly sectioned view; the lower disk 28 is shown in outline only. The same reference numbers denote the same parts as in the preceding embodiment. In this example the upper, fixed disk has only a connection 29 for one mass spectrometer, and passageways 30 and 31 are provided in the disk 27 to connect both concentric circles of connections to the single mass spectrometer by the shortest route. Here again, the angular offset of the connections on the lower disk ensures a sequential connection of the individual gas sampling lines to the mass spectrometer. The disk 27 is installed on the distributor head in place of a disk of the form previously described with two separate passageways and two connections for two mass spectrometers, and one of the two mass spectrometers can communicate with the connection 29 whilst the other mass spectrometer is available for servicing. After servicing, the disk 27 can be replaced with a disk with two passageways (as known from EP-A 0579952). FIG. 8 shows a view of the fixed disk 27 from above, in which the passageways 17,18 and 19,20 are clearly seen.

By providing a sufficient angular offset of the connections and shortened passageways 19,20, it is possible to ensure that eg. the connection on the inner circle of connections does not reach the passageway 20 until the preceding connection on the outer circle has moved away from the passageway 19. In this way, a controlled succession of gas samples is assured, with no intermingling. A blind connection 33 may be provided on the disk for parking the redundant connecting line for a mass spectrometer which is not in use, thus protecting the line from contamination. Instead of the two converging passageways 30 and 31, the disk could be provided with eg. a horizontal link between the passageways 19 and 20, with a link to the connection 29, in an inverted T arrangement.

Instead of mass spectrometers, other testing instruments for gas analysis can of course be provided, eg. pulse fluorescence spectrometers.

Figure 9:
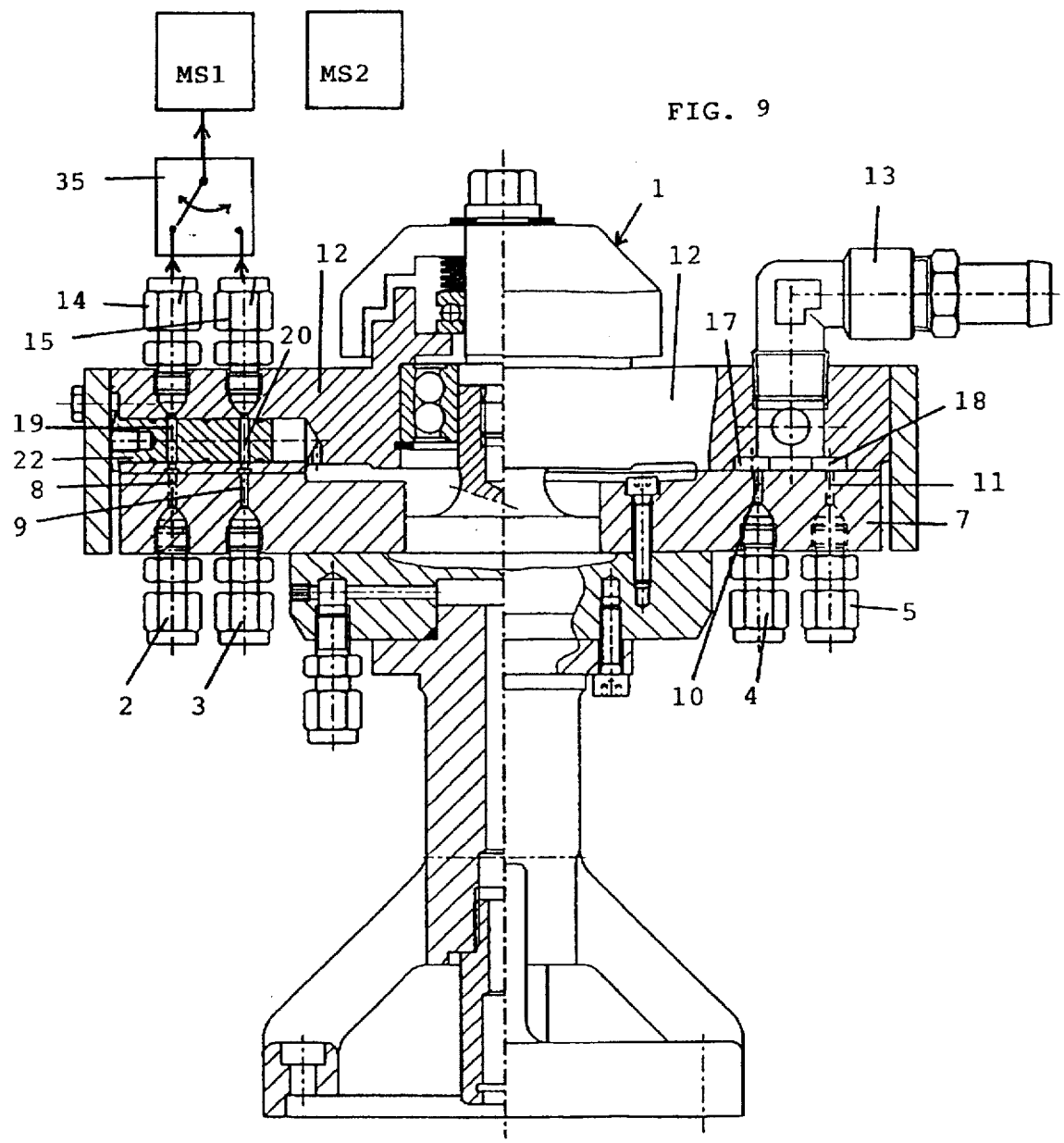
FIG. 9 is a schematic view of a further embodiment.

FIG. 9 shows a variant of the invention in which, instead of a replacement part on the distributor head, an electrically controllable valve 35 is connected between the connections 14 and 15 on the fixed disk 12 and test instrument MS1 (the first mass spectrometer) for the period of repair or servicing of test instrument MS2 (the second mass spectrometer). The valve 35 is in place during the period of repair or servicing, and is subsequently removed, in a similar fashion to the replaceable plug arrangement (the latter is depicted in FIG. 9, but is not needed here; in place of the plug, the fixed disk 12 would in this case extend to the moving disk 7). The gas paths are switched by means of the electrically controllable valve to divert the gas samples from the connections 2,3 alternately to the operative analysing instrument MS1 in a timed (triggered) manner. In place of the valve 35 which is put in place only when the need arises, it is possible to provide a valve arrangement 36 (FIG. 10) which is permanently connected to the connections 14,15 and to the two test instruments, with valves for switching the gas samples to both test instruments or to one test instrument only, as

We claim:

1. Apparatus for the inspection of containers, which are being transported on a carousel conveyor, for the presence of contamination, by testing gas samples from individual containers, comprising:

suction means and sampling probes for removing gas samples simultaneously from a plurality of containers;

a test installation including two test instruments for testing gas samples removed from the containers; and a distributor device for feeding the gas samples in succession from the containers to the test installation, the distributor device being provided coaxially with the carousel conveyor and having a fixed disk and a rotatable disk, the fixed and rotatable disks defining respective passageways and two concentric arcuate paths for transmitting gas samples from the containers to the test instruments, the fixed disk having at least one connection connected to the test installation and another connection connected to the suction means, the sampling probes arranged on a circle around the rotatable disk and alternately connected to the two concentric arcuate paths, a portion of the connecting passageways of the fixed disk being replaced upon the replacement of at least a portion of the fixed disk in order to connect the sampling probes optionally to one test instrument or to two test instruments of the test installation.

2. Apparatus according to claim 1, wherein the fixed disk has an additional connection for a test instrument, and at least one passageway branching from the additional connection to the passageways of the fixed disk.

3. Apparatus according to claim 1, wherein the fixed disk has an inserted, replaceable part with an arrangement of passageways for linking both arcuate paths to which the sampling probes are connected to one test instrument or to two test instruments.

4. Apparatus according to claim 3, wherein the lengths of the passageways arranged in the fixed disk are adjustable.

5. Apparatus according to claim 1, wherein the test installation is a gas analysis unit, and wherein the test instruments comprise mass spectrometers and pulse fluorescence spectrometers.

6. The apparatus according to claim 1, wherein one of the test instruments is a mass spectrometer.

* * * * *